US00PP31953P2

(12) United States Plant Patent
Cantley

(10) Patent No.: US PP31,953 P2
(45) Date of Patent: Jul. 7, 2020

(54) ***NEPENTHES* PLANT NAMED 'CANTNEPDCA'**

(50) Latin Name: ***Nepenthes* hybrid**
Varietal Denomination: CANTNEPDCA

(71) Applicant: Robert Cantley, Hokandara South (LK)

(72) Inventor: Robert Cantley, Hokandara South (LK)

( * ) Notice: Subject to any disclaimer, the term of this patent is extended or adjusted under 35 U.S.C. 154(b) by 0 days.

(21) Appl. No.: 16/501,771

(22) Filed: Jun. 5, 2019

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Nepenthes* cultivar named 'CANTNEPDCA' which is characterized by the combination of a compact plant size, vigorous growth, an elliptical lamina which remains green under almost all cultivation conditions, a dark red cylindrical pitcher, and the stability of these characteristics from generation to generation.

3 Drawing Sheets

Latin name of the genus and species: The Latin name of the genus and species of the novel variety disclosed herein is *Nepenthes* hybrid.

Variety denomination: The inventive cultivar of *Nepenthes* disclosed herein has been given the variety denomination 'CANTNEPDCA'.

BACKGROUND OF THE INVENTION

Parentage: The *Nepenthes* cultivar 'CANTNEPDCA' is the result of a planned breeding program carried out by the inventor at his greenhouse in Samagi Mawatha, Sri Lanka. In January of 2013, the inventor performed a controlled cross-pollination of an unnamed *Nepenthes ampullaria* plant (not patented), the seed parent, with an unnamed *Nepenthes* hybrid plant (not patented), the pollen parent. Both parents were developed and owned by the inventor and were never commercially released. In April of 2013, a seedling that exhibited potential commercial value was selected from all other progeny. The seedling was isolated and allowed to grow to a mature size in order to assess the stability of the unique characteristics for which the candidate was originally selected. In March of 2017, a final selection was made and the new cultivar was given the name 'CANTNEPDCA'.

Asexual Reproduction: Asexual reproduction of 'CANTNEPDCA', by way of meristematic tissue culture, was first performed in the May of 2017 in Samagi Mawatha, Sri Lanka and has since been further cloned using meristematic tissue culture propagation. Through five subsequent generations, the unique features of this cultivar have proven to be stable and true to type.

SUMMARY OF THE INVENTION

The cultivar 'CANTNEPDCA' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CANTNEPDCA'. These characteristics in combination distinguish 'CANTNEPDCA' as a new and distinct *Nepenthes* cultivar:

1. *Nepenthes* 'CANTNEPDCA' exhibits a relatively large plant size; and
2. *Nepenthes* 'CANTNEPDCA' exhibits vigorous growth; and
3. *Nepenthes* 'CANTNEPDCA' exhibits foliage with an elliptical lamina which remains green under almost all cultivation conditions; and
4. *Nepenthes* 'CANTNEPDCA' exhibits foliage with a cylindrical pit-fall pitcher; and
5. *Nepenthes* 'CANTNEPDCA' exhibits a deep red pitcher, devoid a white collar beneath the peristome.

BOTANICAL DESCRIPTION OF THE PLANT

Figure 1:
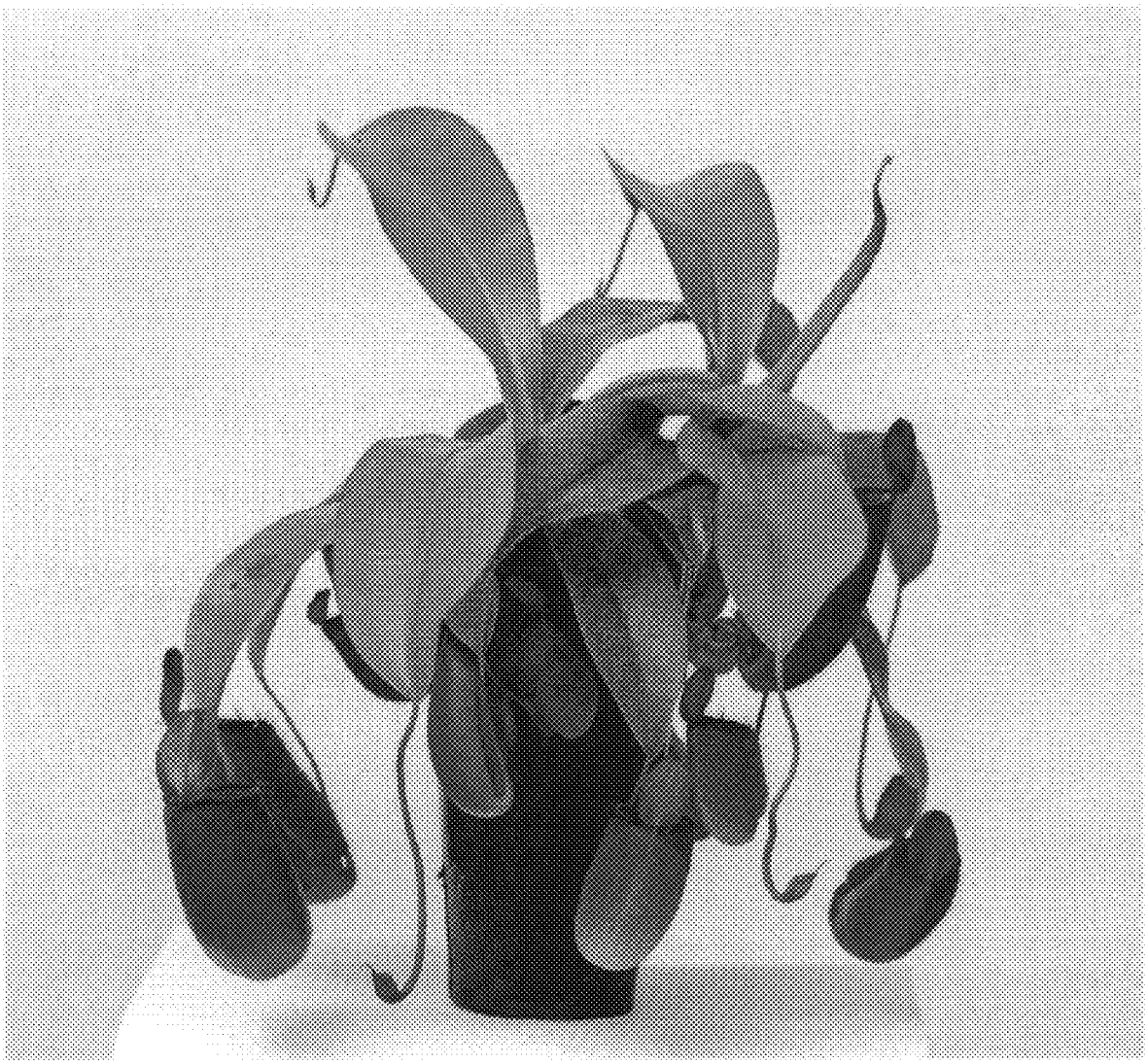
FIG. 1 illustrates, as nearly true as it is reasonably possible to make the same in color photographs of this type, an exemplary plant of 'CANTNEPDCA' grown in a greenhouse in Samagi Mawatha, Sri Lanka. This plant, grown in an 11 cm nursery container, is approximately 12 months old from a rooted young plant.
Figure 2:
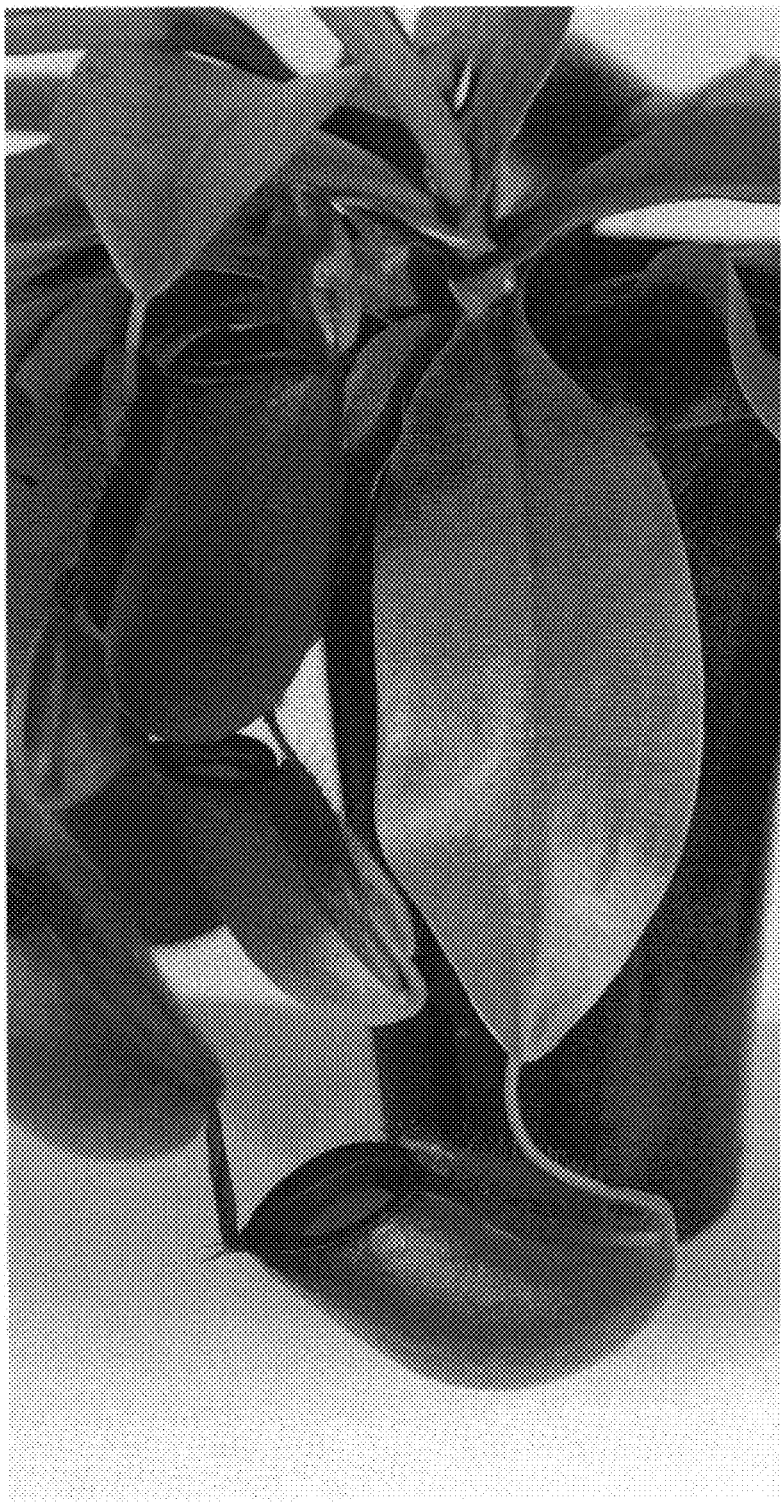
FIG. 2 illustrates, as nearly true as it is reasonably possible to make the same in color photographs of this type, the typical foliage of 'CANTNEPDCA'.
Figure 3:
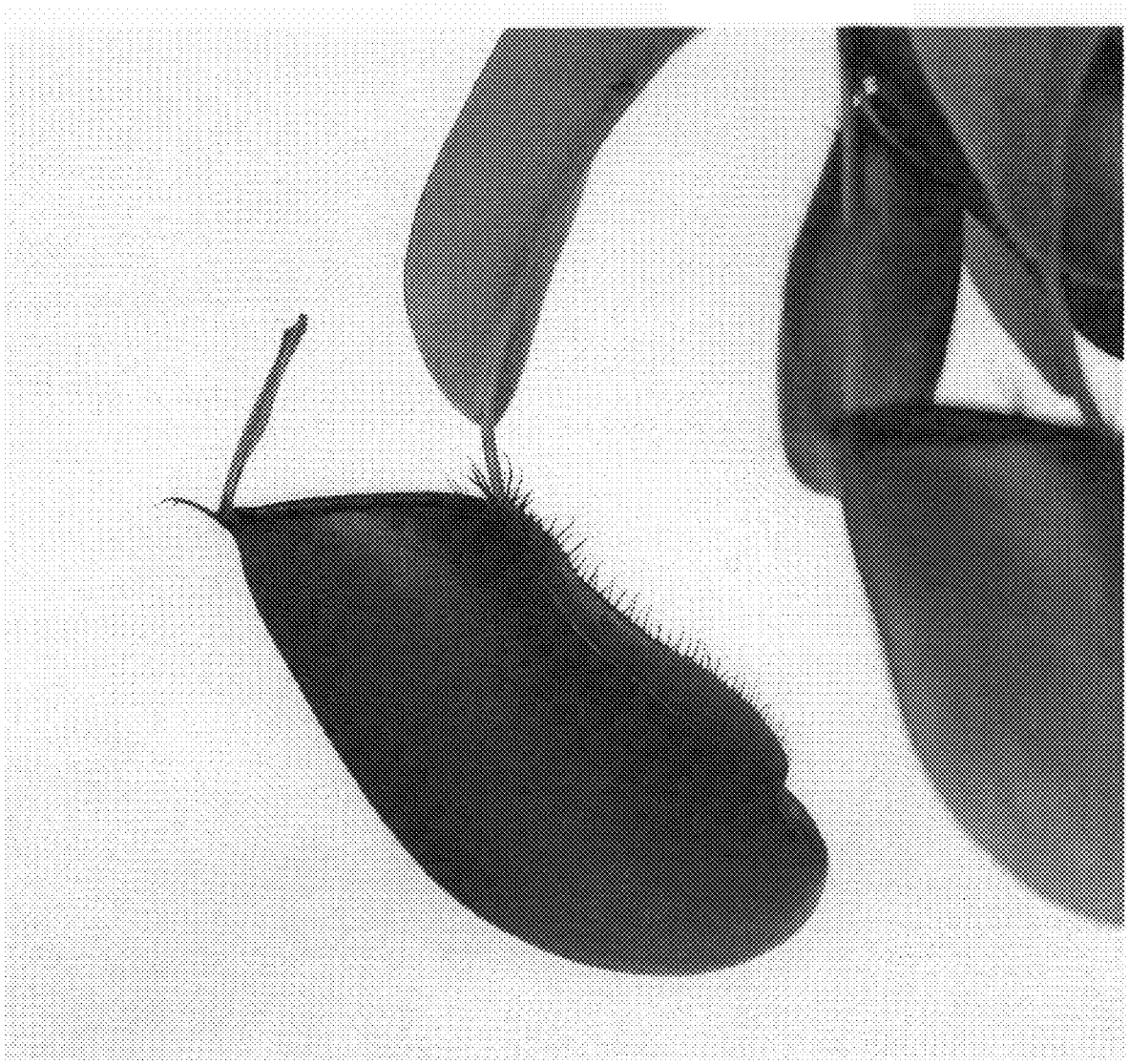
FIG. 3 illustrates, as nearly true as it is reasonably possible to make the same in color photographs of this type, the typical pit-fall pitcher of 'CANTNEPDCA'.

With the exception of the inflorescence and flower descriptions, the following observations and measurements made in April of 2019 describe averages from a sample set of six specimens of 12 month old 'CANTNEPDCA' plants grown in 11 cm nursery pots in a greenhouse in Samagi Mawatha, Sri Lanka. Plants were produced in a greenhouse, under 50 percent shade cloth, using overhead irrigation at regular intervals. Ambient temperatures range from 30 to 35 degrees Celsius during the day and dropped to as low as 17 degrees Celsius at night. No fertilizer or chemical treatments of any kind were utilized.

Those skilled in the art will appreciate that certain characteristics will vary with older or, conversely, with younger plants. 'CANTNEPDCA' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'CANTNEPDCA' and comparisons with the parent plants and most similar commercial *Nepenthes* cultivar known to the inventor are provided below.

Plant description:

*Growth habit.*—Insect-trapping, carnivorous perennial; broad, spreading to upright with epiascidiate leaves that curl downward.

*Plant profile.*—Broad, spreading to upright.

*Average height from base to top of foliage.*—16.0 cm.

*Average height from base to top of the floral plane.*—No flowers have been observed to date.

*Average spread.*—Average of 36.3 cm.

*Growth rate.*—Moderate.

*Plant vigor.*—Moderate.

*Propagation details.*—Asexual propagation is accomplished by way of meristematic tissue culture propagation.

*Time to initiate roots.*—After deflasking the micropropagule, approximately 14 days are required for the propagule to initiate roots at 28 degrees Celsius.

*Time to produce a marketable* 11 *cm potted plant.*—Approximately 10 months.

*Disease and pest resistance or susceptibility.*—Neither resistance nor susceptibility to typical *Nepenthes* rebaudiana pests and diseases has been observed.

*Environmental tolerances.*—Adapt to at least USDA Zones 11 and 12 and temperatures as high as 40 degrees Celsius; moderate to high tolerance to rain; low tolerance to wind.

Root system:

*General.*—A fibrous, moderately dense root system.

*Distribution of roots in the soil profile.*—Moderately branched and moderately deep rooting.

*Diameter.*—0.5 mm.

*Texture.*—Smooth, glabrous.

*Color.*—Black, nearest to RHS 203A.

Stems:

*Branching habit.*—Main stems grow from the base; no lateral branches. Pinching is not required but it will improve branching of main stems.

*Number of main stems per plant.*—2.

*Number of lateral branches per plant.*—0.

*Aspect.*—Rounded; stems formed by decurrent leaf bases.

*Length of lateral branches.*—6.8 cm.

*Diameter of lateral branches.*—Averaging 0.6 cm at the widest point.

*Internode length on lateral branches.*—0.6 cm.

*Pubescence.*—Glabrous.

*Luster.*—Glossy.

*Attitude of lateral branches.*—Average angle is approximately 40 degrees from vertical.

*Strength.*—Strong.

*Color, juvenile.*—Yellow-green, RHS 144A.

*Color, mature.*—Yellow-green, RHS 146B.

*Color at internodes.*—Yellow-green, RHS 146B.

Foliage:

*General description.*—Epiascidiate; a modified leaf that is comprised of a lamina and a pit-fall pitcher structure, connected by a tendril.

*Division.*—Simple.

*Attachment.*—Sessile.

*Arrangement.*—Alternate.

*Attitude.*—Leaves are at an average angle of 60 degrees to the main stem.

*Number of leaves per main stem.*—11.

*Overall dimensions.*—25.9 cm long and 5.5 cm wide.

*Lamina.*—Shape — Narrow elliptic to narrow oblong. Dimensions — 17.7 cm long and 5.5 cm wide, on average. Aspect — Slightly carinate. Attitude — Slightly curled downward. Apex — Acute with the midrib developed into a tendril which attaches the pit-fall pitcher to the lamina. Base — Decurrent. Margin — Entire. Texture and luster of adaxial surface — Smooth and glabrous. Texture of adaxial surface — Smooth and glabrous, with the exception of the midrib which is sparsely covered with very short hairs. Hairs are 0.5 mm in length and colored white, RHS NN155B. Luster of adaxial surface — Glossy. Luster of abaxial surface — Moderately glossy. Color — Juvenile lamina, adaxial surface — Yellow-green, nearest to in between RHS 144A and 152B; margined red, nearest to RNS 46A. Juvenile lamina, abaxial surface — Yellow-green, nearest to RHS 146D, and mottled greyed-red, nearest to RHS 178B; margined red, nearest to RNS 46A. Mature lamina, adaxial surface — Yellow-green, nearest to RHS 144A; narrowly margined greyed-purple, nearest to RNS 183C. Mature lamina, abaxial surface — Yellow-green, nearest to in between RHS 144C and 145D; narrowly margined greyed-purple, nearest to RNS 183C. Venation — Pattern — Pinnate. Color, adaxial surface — Green, nearest to in between RHS 143A and 143B. Color, abaxial surface — Yellow-green, nearest to in between RHS 145B and 150B.

*Tendril.*—Dimensions — 7.6 cm long and 0.2 cm in diameter. Aspect — Rounded. Attitude — Pendulous. Texture and luster — Smooth, glabrous and glossy. Color — Juvenile color, upper surface — Greyed-red, near to RHS 178B. Juvenile color, lower surface — Greyed-red, near to RHS 178B. Mature color, upper surface — Greyed-red, near to RHS 180A, and fading to yellow-green towards the proximal end, nearest to RHS 146D. Mature color, lower surface — Greyed-red, near to RHS 180A, and fading to yellow-green towards the proximal end, nearest to RHS 146D.

*Pit-fall pitcher.*—Shape — Urn-shaped, with a cylindrical pitcher body and an open pitcher lid. Dimensions — 10.9 cm long and 3.5 cm wide, on average. Aspect — Hanging near-vertically.

*Pitcher body.*—Shape — Cylindrical. Texture, outer surface — Moderately covered with very short, adpressed strigose hairs. Hairs have an average length of 0.5 mm and are colored greyed-orange, nearest to RHS N170A. Texture, inner surface — Smooth; glabrous. Luster, outer surface — Matte. Luster, inner surface — Moderately glossy. Pitcher body wings — Two axial ridges (i.e. wings) are present along the back side of the pitcher body. The wings are raised approximately 0.7 cm and are moderately to densely covered with a fringe of hairs that are approximately 0.35 cm long. The wings and hairs are colored greyed-purple, nearest to a mixture of RHS 183A and 187A. Color — Juvenile body, outer surface — Greyed-orange, nearest to RHS 165B. Juvenile body, inner surface — Greyed-orange, nearest to RHS 165B. Mature body, outer surface — Greyed-purple, nearest to in between RHS 183A and 187A, and fading to a mixture of yellow-green and greyed-red towards the bottom of the body, nearest to RHS 148C and 180A. Mature body, inner surface — Yellow-green, nearest to in between RHS 146D and 152D. Juvenile peristome, outer surface — Greyed-orange, nearest to RHS 166A. Juvenile peristome, inner surface — Greyed-orange, nearest to RHS 166A. Mature peristome, outer surface — Nearest to in between red and greyed-purple, RHS 46A and 185A. Mature peristome, inner surface — Greyed-purple, nearest to in between RHS N186C and 187A. Venation — Pattern — Pinnate. Color, outer surface — Greyed-red, nearest to RHS 178B. Color, inner surface — Yellow-green, nearest to in between RHS 146D and 152D.

*Pitcher lid.*—Shape — Elliptic. Dimensions — 2.9 cm long and 2.0 cm wide at the base. Texture, Outer surface — An average of two strigose hairs are present. Hairs have an average length of 0.8 mm and are colored greyed-red, nearest to RHS 180A. Texture, inner surface — Smooth; glabrous. Luster, outer surface — Matte. Luster, inner surface — Moderately glossy. Color — Juvenile lid, outer surface — Greyed-orange, nearest to RHS 165B. Juvenile lid, inner surface — Greyed-orange, nearest to RHS 165B. Mature lid, outer surface — Nearest to in between greyed-purple and brown, RHS N186C and 200A, and becoming greyed-purple towards the center of the lid, nearest the RHS 183B. Mature lid, inner surface — Greyed-purple, RHS 187A, and becoming a darker shade of greyed-purple towards the center of the lid, nearest the RHS 183A. Venation — Pattern — Pinnate. Color, inner surface — Greyed-red, nearest to RHS 178B. Color, outer surface — Yellow-green, nearest to in between RHS 146D and 152D.

Inflorescence: Flowering has not been observed.

Flower buds: Flowering has not been observed.

Flower: Flowering has not been observed.

Reproductive organs: Flowering has not been observed.

Seed and fruit: Not observed to date.

Comparisons with the parent plant: Plants of the new cultivar 'CANTNEPDCA' may be distinguished from its seed parent, an unnamed *Nepenthes ampullaria* plant (not patented), by the characteristics described in Table 1.

TABLE 1

| Characteristic | 'CANTNEPDCA' | The seed parent. |
|---|---|---|
| Rate of growth. | Faster than the seed parent. | Slower than 'CANTNEPDCA'. |
| Plant size. | Larger than the seed parent. | Smaller than 'CANTNEPDCA'. |
| Hardiness. | More hardy; adapt to approximately 10 degrees Celsius. | Less hardy; adapt to approximately 24 degrees Celsius. |
| Pitcher body length. | Longer than the seed parent. | Shorter than 'CANTNEPDCA'. |
| General coloration of the pitcher. | The predominant coloration is a consistent, solid shade of greyed-purple. | Varying shades of greyed-purple and red. |

Plants of the new cultivar 'CANTNEPDCA' may be distinguished from its pollen parent, an unnamed *Nepenthes* hybrid plant (not patented), by the characteristics described in Table 2.

TABLE 2

| Characteristic | 'CANTNEPDCA' | The pollen parent. |
|---|---|---|
| Pitcher body size. | Smaller than the pollen parent. | Larger than 'CANTNEPDCA'. |
| General coloration of the pitcher. | The predominant coloration is a consistent, solid shade of greyed-purple. | Green with light red markings. |

Comparison with the most similar *Nepenthes* cultivar known to the inventor: Plants of the new cultivar 'CANTNEPDCA' are most similar to the commercial variety, *Nepenthes* 'Bloody Mary' (not patented). A comparison of 'CANTNEPDCA' with 'Bloody Mary' is described in Table 3.

TABLE 3

| Characteristic | 'CANTNEPDCA' | 'Bloody Mary' |
|---|---|---|
| General coloration of the foliage. | Foliage generally remains green under most conditions. | Juvenile foliage becomes suffused with red when provided sufficient light. |
| Lamina shape. | Elliptical. | Linear. |
| Pitcher body size, relative to the lamina. | Exhibits a greater pitcher-length to lamina-length ratio. | Exhibits a lesser pitcher-length to lamina-length ratio. |
| Pitcher body shape. | Cylindrical. | Ellipsoidal. |
| Presence of a narrow white collar beneath the peristome, which ages to a black. | Generally absent. | Present. |

That which is claimed is:

1. A new and distinct cultivar of *Nepenthes* plant named 'CANTNEPDCA', substantially as described and illustrated herein.

* * * * *